United States Patent [19]
Rosenbaum et al.

[11] Patent Number: 5,766,012
[45] Date of Patent: Jun. 16, 1998

[54] DENTAL ETCHANT AND PROCESS OF USING

[76] Inventors: Michael Rosenbaum, 457 Leah Dr., Fort Washington, Pa. 19034; Milton Richlin, 829 Finch Dr., Bensalem, Pa. 19020; Alan J. Braverman, 1468 Fort Washington Ave., Ambler, Pa. 19002

[21] Appl. No.: 846,182

[22] Filed: Apr. 28, 1997

[51] Int. Cl.$^6$ .................................................. A61C 5/00
[52] U.S. Cl. .................................................. 433/228.1
[58] Field of Search ........................... 433/9, 215, 217.1, 433/222.1, 226, 228.1

[56] References Cited

U.S. PATENT DOCUMENTS

| | | | |
|---|---|---|---|
| 4,204,978 | 5/1980 | Ibsen et al. | 252/408 |
| 4,678,436 | 7/1987 | Kondo et al. | 433/228.1 |
| 4,966,828 | 10/1990 | Doenges et al. | 430/281 |
| 5,216,158 | 6/1993 | Pawlowski et al. | 544/216 |
| 5,256,065 | 10/1993 | Nicholson | 433/228.1 |

*Primary Examiner*—Nicholas D. Lucchesi
*Attorney, Agent, or Firm*—Paul Lipsitz

[57] ABSTRACT

An improved dental etchant and a process for using it which comprises a phosphoric acid etchant containing a colorant which changes color at a pH of about 2.5.

10 Claims, No Drawings

DENTAL ETCHANT AND PROCESS OF USING

FIELD OF THE INVENTION

This invention relates to an improved acid etchant for use on tooth enamel, dentin, and cementum (hereinafter referred to as "tooth structure" or "tooth surface") as a preparation to the tooth surface for conventional dental composite bonded restorations, pit and fissure sealants, cementation of prosthetic restorations, porcelain veneers, and bonding of orthodontic appliances.

BACKGROUND OF THE INVENTION

In the preparation of teeth for conventional dental composite bonded restorations, pit and fissure sealants, cementation of prosthetic restorations, porcelain veneers, and bonding of orthodontic appliances, it is necessary to prepare the desired tooth surface. The standard method is a technique whereby the cleaned and dried tooth surface is treated with an acidic etchant solution or gel. Application of the etchant for a short period of time (approximately one minute) on the tooth surface to be treated, followed by a thorough water rinse and air drying, produces a selective dissolution of the tooth surface to promote an effective bond with the subsequently applied restorative bonding agent or materials. The acid removes calcium salts which increases the size and number of the microspaces. The bonding agent fills these "tags" and is then polymerized to produce the mechanical interlocking of resin to tooth.

Two problems associated with this acid etching method are 1) difficulty in knowing just when the etchant has been sufficiently effective to provide adequate bond strength, and 2) excessive etching, which would damage the surface tooth structure and/or dental pulp. Commercial etchants usually are used for 30 to 60 seconds on enamel. The solubility of enamel can vary depending on the surface of tooth, type of tooth, and numerous other variations from person to person. Dentin and cementum should be etched for 10 to 15 seconds because these tooth structures contain less calcified material and are more porous. The pulpal tissues of the tooth can be traumatized if dentin or cementumi is etched too much. Also, dentin and cementum can have many variations in solubility which makes it difficult to know when optimum etching has occurred.

This invention provides an improved etchant gel which more precisely indicates to the dental practitioner when a consistent and optimal dissolution of tooth surface has been achieved, thereby avoiding failure of the procedure and damage to the tooth.

BRIEF DESCRIPTION OF THE INVENTION

In accord with the invention, an acid etchant gel for tooth structure is provided which comprises a tooth acid etchant containing a pH sensitive colorant which, when applied to the tooth stucture, displays a readily observed color change to indicate that a consistent and optimum etch has occurred. This invention also provides an improved process for acid etching tooth structure wherein the improved etchant of the invention is used.

DISCUSSION OF PRIOR ART

An article by S. Buchan and R. W. Peggie in the Journal of Dental Research, July–August, 1966, page 1120–1129 (Chem. Abs., Vol. 66, 22196h, 1967), discloses the use of a colorant in an alginate dental impression composition to measure setting times with a decrease in pH values. The colors obtained are said to "merely indicate the pH of the aqueous phase of the paste at successive stages in the mixing, loading, and insertion cycle and are obtained by incorporating appropriate chemical indicators."

DETAILED DESCRIPTION OF THE INVENTION

As stated above, the invention provides an improved tooth enamel etchant comprising an etchant gel containing a pH sensitive colorant which changes color when optimum and consistent etching of the tooth enamel has occurred. A preferred conventional etchant is of the phosphoric acid type, such as is disclosed in U.S. Pat. No. 5,256,065. The amount of phosphoric acid in the etchant solution or gel may be between about 10)% and about 20% by weight of the solution or gel. The concentration of colorant in the gel is quite low and will normally be between about 0.001% an about 0.05% based on the weight of the gel. Preferably an amount of from about 0.002% to about 0.02% of colorant will be used.

The application of the acid gel to tooth structure produces a selective dissolution of the tooth surface to promote an effective bond with the subsequently applied restorative bonding agent or materials. The acid removes calcium salts which increases the size and number of the microspaces. The bonding agent fills these "tags" and is then polymerized to produce the mechanical interlocking of resin to tooth. It has been determined that in order to obtain optimum bonding, the amount of calcium salts dissolved from the tooth is such that the initial pH of the gel (about 0.5 or lower) must increase to about 2.5. Thus, any colorant (i.e., a pH indicator) incorporated in the gel should show a relatively sharp color change at a pH of about 2.5 or somewhat lower. Thus, useful colorants are those showing a color change from about 2.0 to about 2.5. Further, the colorant should have low toxicity, but since the colorant-containing gel produces excellent results at very low concentrations, and is washed from the tooth and aspirated from the mouth during treatment, toxicity is not a significant factor. However, as in the use of any routine dental material, the etchant should be used with all proper isolation and protection barrier techniques to reduce the risk of oral ingestion and skin or eye contact.

While any colorant meeting the above criteria for color change and low toxicity is operable in the invention, preferred colorants are methyl violet, crystal violet and ethyl violet.

As indicated, the acid etchant gels used in the invention will usually contain from about 10% to about 20% by weight of the gel of phosphoric acid ($H_3PO_4$). When the gel is to be used to etch dentin, the acid concentration is usually at the lower concentrations, e.g., about 10%. When etching tooth enamel, however, an acid concentration in the gel of about 10% to about 15% is preferred. It will be understood that there will be variations in the times at which the color change will occur depending upon the combination of acid concentration in the gel and the amounts and types of colorants used. However, the process of the invention employs a color change, not a time interval, to determine when the restorative should be applied and that is a significant advantage of the invention.

On application of the indicator-containing gel to the dentin of the tooth, a color change to violet will occur within a few seconds. Upon application to tooth enamel, however, the color change occurs in about one minute to about two minutes. When this change is noted by the dentist, the tooth is ready to be washed, dried and the restorative material applied.

The restoratives used are conventional and include such agents as cyanoacrylates, polyurethanes, and bis-phenol-A-glycidyl methacrylate, all of which are commercially available.

EXAMPLES

EXAMPLE 1 (Conventional Method)

A phosphoric acid gel such Scotchbond™ Etchant (a trademark of 3M Company) is applied to the enamel area of a tooth to be treated with a soft-bristle fine-tipped brush. Application time is usually 15 to 20 seconds, but for fluorosed or deciduous enamel the time is usually increased to one minute.

After the etching period, the enamel surface is thoroughly cleansed with a copious water wash for at least 15 to 30 seconds to remove containment residues consisting mostly of soluble calcium salts.

The treated tooth structure is then dried, preferably with a suitable warm air dryer after which the surface has a chalky white opaque appearance and is ready for application of the restorative by conventional methods.

EXAMPLE 2 (Method of the Invention)

The general procedure of Example 1 is followed, but the etchant gel contains 20% by weight of phosphoric acid and .023% of crystal violet. The crystal violet added to the gel was prepared to contain 0.75% of the colorant in 1 to 1 by weight mixture of water and 200 proof ethanol.

When the colorant-containing gel applied to the dentin changes from green to violet, the etchant is removed with a water wash, dried and the restorative applied.

Application of a conventional restorative (Scotchbond™ multipurpose bonding adhesive) to the etched tooth enamel proceeds in the normal manner and yields a very satisfactory result.

EXAMPLE 3

Following the procedure of Example 2, a 15% phosphoric acid gel containing 0.007% methyl violet is applied to the enamel area of a tooth. The gel changes color to violet after one minute at which point the treated tooth is ready for washing, drying and application of the restorative.

EXAMPLE 4

Using a 15% phosphoric acid gel, as in Example 3, but with various amounts of methyl violet and applying the colorant-containing gel on both dentin and enamel, the following results are obtained:

|  | Time For Color Change | |
| --- | --- | --- |
| Percent Colorant Concentration | Applied to Dentin | Applied to Enamel |
| 0.002 | 34 seconds | no change |
| 0.005 | 30 seconds | 1.5 minutes |
| 0.012 | 15.45 seconds | 1.5 minutes |
| 0.016 | 15 seconds | 2.0 minutes |
| 0.025 | 20 seconds | 1.5 minutes |

EXAMPLE 5

Following the procedure of Example 3, but using a 10% phosphoric acid gel and various amounts of crystal violet as colorant, the following times for color change are obtained:

|  | Time For Color Change | |
| --- | --- | --- |
| Percent Colorant Concentration | Applied to Dentin | Applied to Enamel |
| 0.004 | 15 seconds | 1.75 minutes |
| 0.010 | 15 seconds | 1.0 minutes |

We claim:

1. An improved dental etchant composition comprising phosphoric acid as an active etchant and a colorant, wherein said colorant changes color at a pH of about 2.5 wherein said etchant is a gel which contains from about 10% to about 20% by weight of said gel of phosphoric acid and said colorant contained in said gel is in an amount of from about 0.001% to about 0.05% by weight of said gel.

2. The etchant of claim 1 wherein said colorant is methyl violet.

3. The etchant of claim 1 wherein said colorant is crystal violet.

4. The etchant of claim 1 wherein said colorant is ethyl violet.

5. The etchant of claim 1 wherein the amount of colorant is from about 0.002% to about 0.02%.

6. In the process of etching a tooth with phosphoric acid for a subsequent dental operation, the improvement of employing a phosphoric acid etchant containing a colorant which changes color at a pH of about 2.5; comprising the steps of applying said colorant-containing phosphoric acid etchant to said tooth, maintaining said etchant on said tooth until a color change occurs, and thereafter removing said etchant.

7. The process of claim 6 wherein said etchant is a gel which contains from about 10% to about 20% by weight of said gel of phosphoric acid and said colorant in said gel is in an amount of from about 0.001% to about 0.05% by weight of said gel.

8. The process of claim 7 wherein said colorant is from about 0.002% to about 0.02%.

9. The process of claim 8 wherein the colorant is methyl violet.

10. The process of claim 8 wherein the colorant is crystal violet.

* * * * *